United States Patent [19]
Dixon et al.

[11] Patent Number: 5,357,967
[45] Date of Patent: Oct. 25, 1994

[54] METHOD AND APPARATUS FOR MEASURING FLOW USING FREQUENCY-DISPERSIVE TECHNIQUES

[75] Inventors: Robert Dixon, Palmer Lake, Colo.; Theodore R. Lapp, Mission Viejo; Donald E. Bobo, Jr., Orange, both of Calif.

[73] Assignee: Baxter International Inc., Deerfield, Ill.

[21] Appl. No.: 71,838

[22] Filed: Jun. 4, 1993

[51] Int. Cl.$^5$ .............................. A61B 5/029
[52] U.S. Cl. .................... 128/691; 128/713; 128/736
[58] Field of Search .......... 128/668, 691–692, 128/694, 736, 713

[56] References Cited

U.S. PATENT DOCUMENTS

| | | | |
|---|---|---|---|
| 4,236,527 | 12/1980 | Newbower et al. | 128/692 |
| 4,502,488 | 3/1985 | Degironimo et al. | 128/692 |
| 4,507,974 | 4/1985 | Yelderman | 73/861.06 |
| 5,217,019 | 6/1993 | Hughes | 128/668 |

OTHER PUBLICATIONS

"Continuous Thermal Measurement of Cardiac Output", Philip, Long, Quinn, & Newbower, -IEEE Transations of Biomedical Engineering, vol. BME-31, No. 5, May 1984, pp. 393–400.

"Spread Spectrum Systems", Dixon, A Wiley-Interscience Publication 1984, pp. V, 45–47.

Primary Examiner—Angela D. Sykes
Attorney, Agent, or Firm—Jeffrey Slusher; Bruce M. Canter

[57] ABSTRACT

A system for measuring fluid flow within a conduit, such as blood flow from the heart, includes a heating element that is driven so as to apply heat to the fluid at an upstream position as a series of periodic heat signals. A temperature sensor located downstream measures a local temperature of the fluid and generates an electrical fluid temperature signal corresponding to the local temperature. This signal is then applied to a dispersive filter, which outputs a pulse-like signal in the presence of each periodic heat signal. Fluid flow is then calculated by a processor as a function of the area under an estimated impulse response curve for the channel in which the fluid flows. Each periodic heat signal is preferably sinusoidal and has an instantaneous frequency that varies substantially continuously between a first frequency and a second frequency over a pre-determined active input signal period. In a preferred embodiment, the frequency varies linearly between a first and a second frequency over a predetermined time period. The output signal from the filter, which is itself an estimate of the channel impulse response, is preferably integrated in order to provide a parameter estimate that is inversely proportional to flow. The corresponding method of measuring fluid flow using a frequency-swept input heat signal and matched dispersive filtering is included.

17 Claims, 17 Drawing Sheets

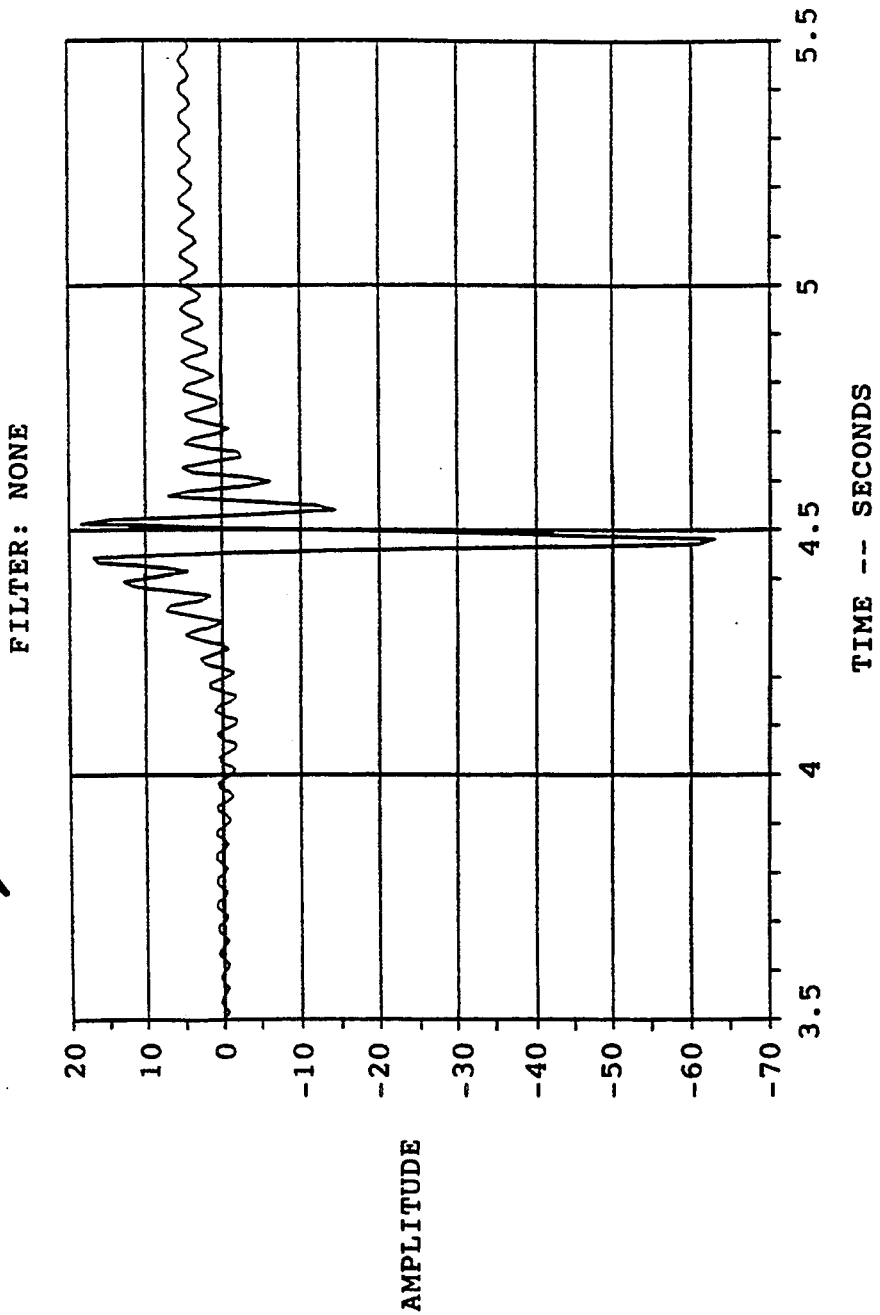

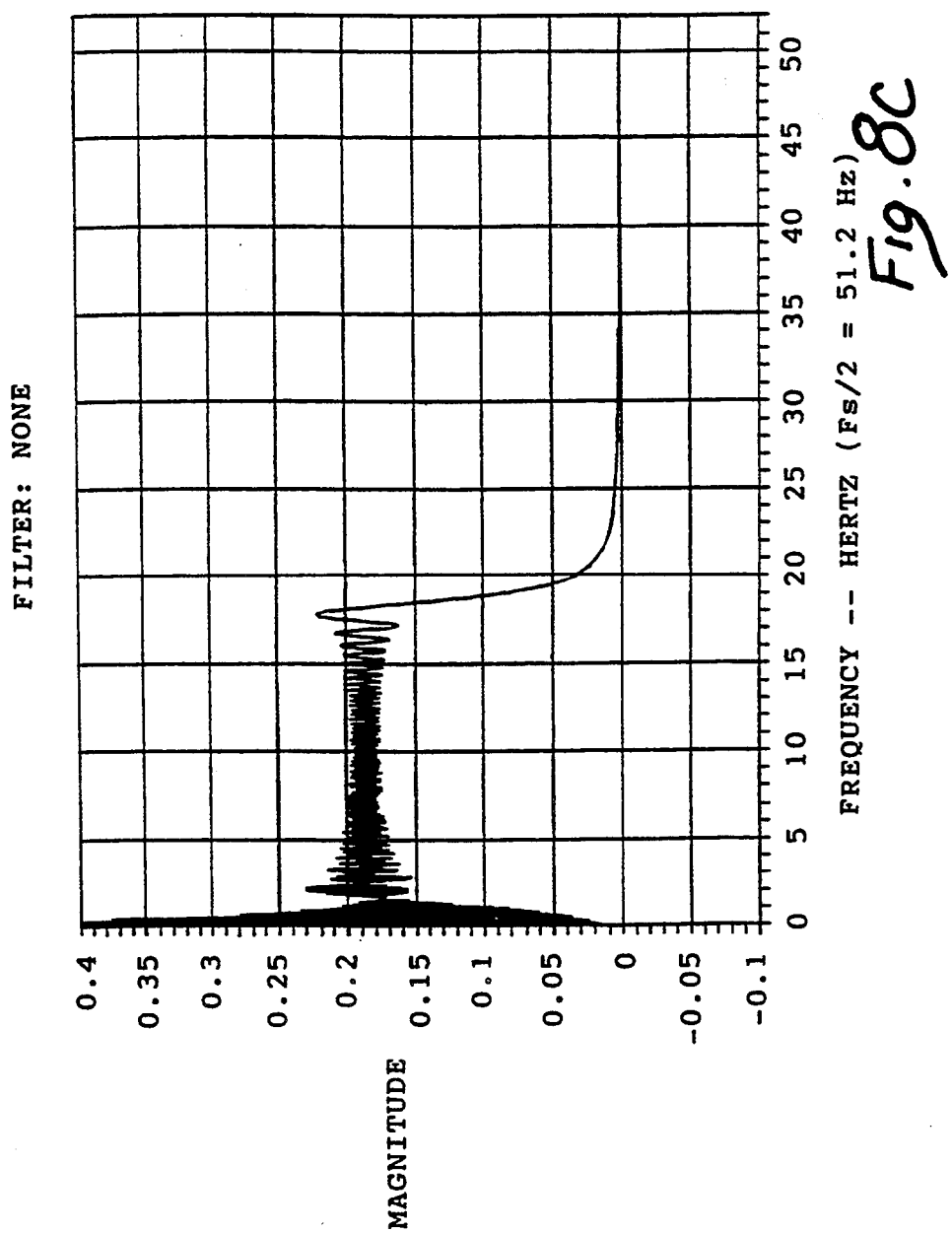

METHOD AND APPARATUS FOR MEASURING FLOW USING FREQUENCY-DISPERSIVE TECHNIQUES

BACKGROUND OF THE INVENTION

1. Technical Field

This invention relates to a method and an apparatus for measuring the volume of flow of a fluid through a conduit, especially the flow of blood from the heart.

2. Description of Related Art

The ability to measure the volume of fluid flow in conduits is important in many different types of applications. Such applications range from measuring the amount of oil that flows through a pipeline to measuring the volume of blood that the heart is pumping.

The measure of volumetric flow of blood from the heart presents particular problems. First, the flow of blood in the vascular system is generally non-uniform. Second, the measurement device used should obviously not be more intrusive than necessary, not only to avoid reducing the accuracy of measurements but also to avoid interfering with the normal operation of the heart; otherwise, the measurement process itself may be more dangerous for a patient than any condition the measurement system is intended to discover. Third, the accuracy of measurement systems for cardiovascular flow suffers from the presence of often pronounced disturbances such as the periodic, pulsating nature of the flow and other frequency-related disturbances such as are caused by the breathing of the patient.

Because cardiac output is often a very important diagnostic indicator, there are a large number of devices for measuring blood flow in the vascular system. In many passive measurement systems, some irregular indicator such as variations in optical translucence or magnetic irregularities are observed at two points in the blood vessel. Using auto- and cross-correlation techniques, blood flow is estimated as a function of blood velocity, which is in turn derived as a product of the correlation technique.

In active measurement systems, the indicator is injected into or is applied to the bloodstream, whereupon blood flow is determined as in passive systems either by direct measurement of the time it takes for some quantity of the indicator to pass between two measurement points, or by using some correlation technique. The indicators used in such systems include actual substances such as dyes and radioactive particles, and pure-energy indicators such as ultrasound and heat.

U.S. Pat. No. 4,507,974 (Yelderman, 2 Apr., 1985), and U.S. Pat. No. 4,236,527 (Newbower et al., 2 Dec., 1980), describe systems for measuring cardiac output in which heat is used as an indicator. In such heat-based systems, a balloon catheter is typically threaded down through the right jugular vein, and lodges proximal to the branch of the pulmonary artery via the right atrium and the right ventricle. The catheter includes a resistive heating element, which is positioned in the atrium and/or ventricle, and a thermistor, which is positioned in the artery.

In the Newbower system, the heating element is energized in such a way that the thermal energy applied to the surrounding blood has at least two frequency components, either a fundamental and one or more harmonics, or as a square-wave signal, which can also be resolved into a fundamental frequency and a number of harmonics. The temperature of the blood downstream is then measured by the thermistor and the corresponding electrical signal is filtered with respect to the fundamental frequency and at least one other frequency. Cardiac output is then estimated based on an approximate reconstruction of the transfer function of the local vascular system.

The Yelderman system energizes the heater according to a pseudo-random sequence of square waves that are derived based on a binary maximum length sequence. Correlation techniques are then used to extract from the thermistor signal an estimate of the flow rate of blood from the heating element to the thermistor.

Because the thermal noise in a vascular system is typically great, especially in and near the heart, the problem of a low signal-to-noise ratio reduces the efficiency of many heat-based measurement systems such as the Newbower and Yelderman systems. In other words, the information-carrying heat signal may, to a greater or lesser extent, be "drowned out" by the variations in temperature produced by the vascular system itself.

A seemingly obvious way to increase the signal-to-noise ratio and improve the efficiency of the measurement system would be simply to increase the power of the signal itself. In the context of heat-based systems for measuring cardiac output, this means increasing the heat generated by the heating element. This approach is, however, often impractical or impossible in systems for measuring cardiac output, since tissue or blood damage could result if the local blood temperature rises too far above normal; for example, temperatures above 50° C. would almost always cause some damage.

A second problem that affects frequency-based detection systems is that there are strong natural frequency components of the body itself in the frequency range in which heat-based systems typically operate. For example, if the patient's ventilation frequency (either natural or mechanically induced) is 0.2 Hz and the excitation frequency of the heating element is also 0.2 Hz, the downstream filtering and correlation system may not be able to distinguish between the two sources and the estimate of blood flow may become unreliable.

One way to counteract this problem is to include several different frequency components in the heat signal injected into the blood. Using the Newbower system, for example, one preferably selects the fundamental frequency of the injected heat signal such that it is located at a noise minimum in the noise profile of the cardiac system. One drawback of such an approach is that one must know what frequency range contains the noise minimum in order to tune the system. Furthermore, it is difficult or impractical to modulate blood temperature at frequencies well above any significant "noisy" frequency range while keeping the system within the power and size limitations dictated by its use in the heart.

The pseudo-random square-wave heat signals used in the Yelderman system alleviate some of the problems of frequency selection in a "non-noisy" range by generating the heat signal itself to have several frequency components of approximately the same amplitude with approximately equal spacing within a frequency band. This increases the likelihood that at least some of the frequency components are in a "non-noisy" range. Moreover, the correlation techniques used in the Yelderman system typically will reject noise better than the conventional filters used in the Newbower system.

One shortcoming of the pseudo-random technique used by Yelderman is that the average power of the signal applied to the blood is only approximately half the peak power, that is, the pseudo-random signal has a duty-cycle of approximately fifty per cent. An additional weakness of the pseudo-random technique is that the number of fundamental frequency components generated is no greater than the number of steps in the maximum length sequence used. For example, assume that the pseudo-random generator generates a sequence of length 15 with a period of 10 seconds. At most 15 fundamental frequency components can then be generated in the frequency range of 0.1 Hz–10 Hz.

The pseudo-random excitation signal is an approximation to a signal that has a continuous and flat spectrum within a given frequency range. A flat spectrum, or at least a large number of significant frequency components in a given frequency range, is desirable since the more frequency components a signal has that do not correspond to a frequency in the noise spectrum, the easier it will generally be to detect the signal in the presence of the noise.

Yet another drawback of systems that assume the use of a square-wave heat signal is that it requires a relatively high amount of power to cause a heating element's temperature to rise and fall sharply enough to approximate the rising and falling edges of the square-wave. Even if one were to implement such a heating element, the thermal properties of the blood, which must be taken as they are, make it even more difficult to realize the intended-square wave signal shape.

Problems similar to those just described with respect to measuring cardiac output are also encountered measuring the flow of fluids other than blood. What is needed is therefore a system and a method for measuring fluid flow that has a lower peak-to-average power ratio than systems such as the known pseudo-random excitation system, that do not require rapid temperature changes in the fluid, that are relatively easy to implement, that effectively avoid disturbance frequencies, and that can realize a relatively high signal-to-noise ratio. The system and method should ideally be suitable for use within the vascular system to measure cardiac output. It is the object of this invention to provide a system and a method that meet these goals.

SUMMARY OF THE INVENTION

According to the invention, a system for measuring fluid flow within a conduit includes a heating element that is driven so as to apply heat to the fluid at an upstream position as a series of periodic heat signals. A temperature sensor located downstream measures a local temperature of the fluid and generates an electrical fluid temperature signal corresponding to the local temperature. This signal is then applied to a filter, which outputs a pulse-like signal in the presence of each periodic heat signal. Fluid flow is then calculated by a processor as a function of the area under the filter output signal.

Each periodic heat signal is preferably sinusoidal and has an instantaneous frequency that varies substantially continuously between a first frequency and a second frequency over a pre-determined active input signal period. In a preferred embodiment, the frequency varies linearly between a first and a second frequency over a predetermined time period. The periodic heat signals may also include inactive or "quiet" partial periods, in which no additional heat is applied to the fluid.

In a preferred embodiment, the heating element is resistive, and a drive circuit, which is connected to and controlled by the processor, drives the heating element. The processor may also include a memory that stores parameters for the temperature profile of the heating element, including non-linear profiles.

The temperature sensor is preferably a thermistor, which is connected, via amplification or other signal conditioning circuitry, to the filter. In a preferred embodiment of the invention, the output signal from the filter is integrated in order to estimate the area under the channel impulse response, which is shown to be inversely proportional to flow.

A preferred application of the invention is as a tool to measure cardiac output. In this application, the heating element and thermistor are mounted in a catheter. The heating element is then positioned within the right atrium and/or right ventricle of a patient, and the thermistor is positioned proximal to the branch of the pulmonary artery.

For periodic heat signals with a linearly varying frequency characteristic, the filter preferably has a frequency response with substantially constant amplitude between the first and second frequencies and a substantially linear delay characteristic between the first and second frequencies.

The invention also encompasses a method according to which the fluid, for example blood, is heated at an upstream position according to a periodic heat profile signal that is sinusoidal and has an instantaneous frequency that varies substantially continuously between a first frequency and a second frequency over a pre-determined active input signal period. The local downstream temperature of the fluid is then sensed and an electrical fluid temperature signal corresponding to the local temperature is then generated. This signal is then applied to a dispersive filter whose output, preferably after integration, is used to calculate fluid flow.

BRIEF DESCRIPTION OF THE DRAWINGS

FIGS. 8a, 8b, and 8c are plots of the temporal and spectral characteristics of a simulated output signal from the invention after the input signal has passed through a simulated channel with all-pass characteristics.

DETAILED DESCRIPTION

Figure 1:
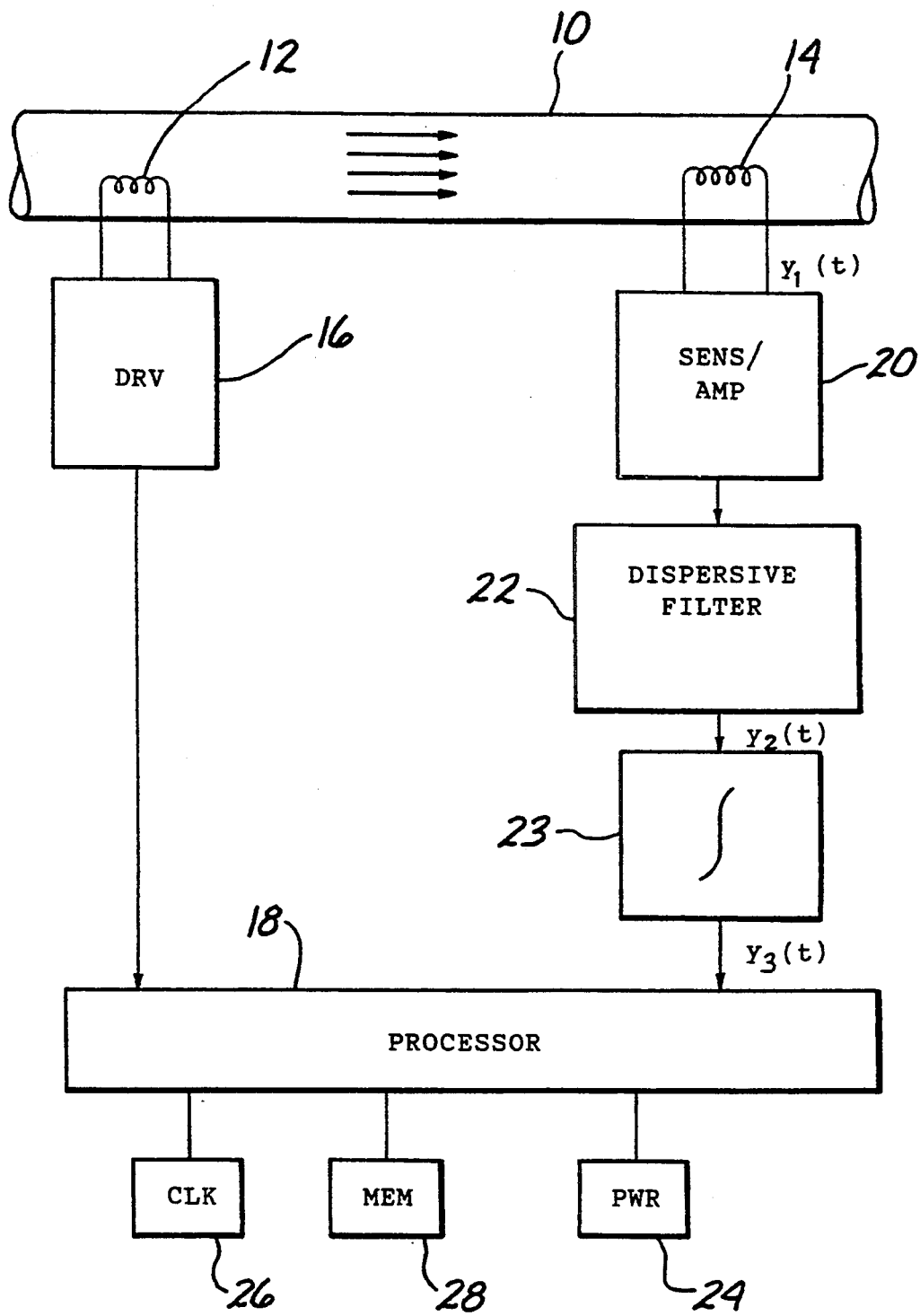
FIG. 1 is a block diagram of a system according to the invention for measuring fluid flow within a conduit.

FIG. 1 is a block diagram of the system according to the invention for measuring fluid flow. The invention may be used for measuring the flow of any fluid within a defined volume, but, as is described below, it is particularly advantageous for measuring cardiac output. The invention is therefore described below primarily with reference to measurement of cardiac output.

In FIG. 1, fluid such as blood flows through a conduit or other vessel 10. A heating element 12 is positioned upstream in the vessel 10 and a thermistor or similar temperature-sensing element 14 is located downstream from the heating element 12. The heating element 12 is preferably an electrically resistive element whose temperature is determined by the current or voltage supplied to the element via a driving circuit 16, which applies electrical current or voltage to the heating element 12 based on a temperature profile generating circuit such as a processor 18. The processor 18 may be either a conventional or a customized microprocessor or other integrated circuit that generates a temperature profile with characteristics described below.

The thermistor 14 is electrically connected to a sensing and amplification circuit 20, which may be a conventional circuit whose electrical output voltage is a predetermined function of the temperature sensed by the thermistor 14. The output from the sensor and amplification circuit 20 is applied to a dispersive filter 22, whose output is integrated by a conventional integration circuit 23 and is then connected to the processor 18.

Power to the system, including the processor 18, is derived from a conventional power source 24. A conventional timing signal is provided for the processor 18, preferably by a known clock circuit 26. A conventional memory circuit 28 is also included for storage of the program according to which the processor 18 operates. As is described below, the heating element 12 may be energized in such a way that it follows a specialized temperature profile, and in such case the memory circuit 28 may also optionally be used to store either a numerical representation of the profile or the parameters necessary for the processor 18 to generate the profile.

As is well known in the art of digital design, the processor 18 may itself include the clock circuit 26 and the memory circuit 28. Depending on the application, the processor 18 may also be used to implement the dispersive filter 22 and the integrator 23.

When the invention is used to measure cardiac output, the heating element and the thermistor are preferably mounted in a catheter. In the usual manner, the catheter is then preferably fed into the patient's jugular vein, passes through the right atrium and right ventricle of the patient's heart, and then out through the pulmonic valve into the patient's pulmonary artery. If a balloon-type catheter is used, the balloon, which is located at the distal end of the catheter, is then inflated to hold the catheter is proper position. When in position, the heating element preferably extends from the right atrium to the right ventricle, across the tricuspid valve. Measured from the distal end of the catheter, the heating element preferably extends from about the 14 cm position to about the 25 cm position. The thermistor is preferably positioned proximal to the branch of the pulmonary artery.

Figure 2:
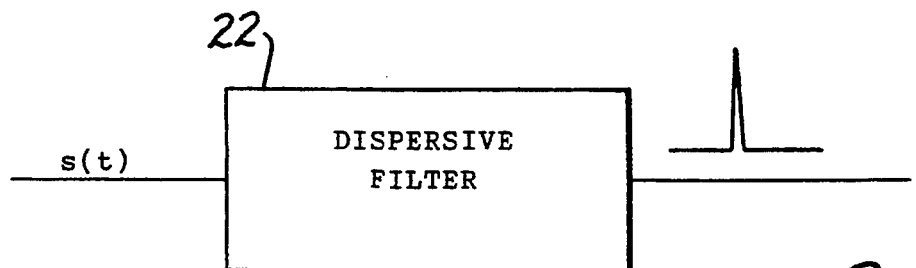
FIG. 2 illustrates the general characteristic of a dispersive filter used in the flow measurement system according to the invention.

FIG. 2 illustrates the general nature of the dispersive filter 22 used in this invention. For an input signal s(t) having the proper characteristics (described below), the output from the dispersive filter 22 will approximate a "pulse," which represents compression of the energy in the input signal s(t).

Figure 3A:
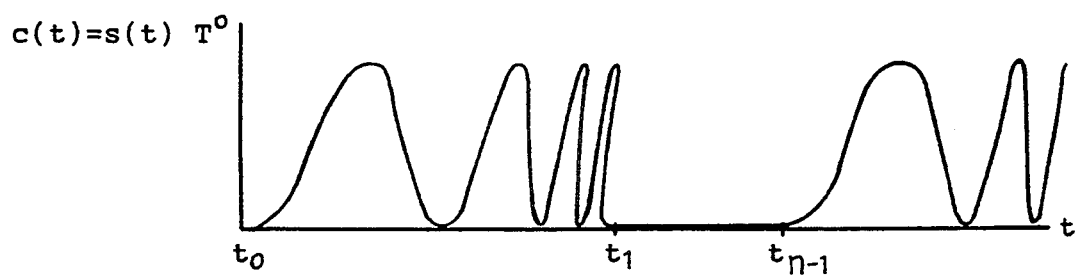
FIGS. 3a and 3b illustrate, respectively, the time and frequency characteristics of one example of a heat input signal used in a preferred embodiment of the invention.

FIG. 3a illustrates one example of an input or excitation profile used in the preferred embodiment of the invention. As FIG. 3a shows, the excitation signal c(t), which corresponds to the temperature of the heating element 12 (see FIG. 1), is generally sinusoidal with a period equal to $T=(t_1-t_0)$ and a continuously varying frequency.

The spectrum of c(t) is approximately rectangular with a second-order phase characteristic $\phi(f)$. In other words, the delay, $\Delta$, versus frequency, f, curve is linear:

$$\Delta(f) \propto f$$

$$\phi(f) = \int \Delta(f) \propto f^2$$

For ease of implementation, the frequency of the input signal preferably varies linearly, in which case it may be expressed as:

$$c(t) = A_{max} \cos\{2\pi \cdot f(t) \cdot t + \Phi\} \quad (1)$$

where $f(t) = f_0 + t \cdot df/dt$ $f_0$ = initial frequency t = measurement time after $t_0$; $t_0 \leq t \leq t_1$ df/dt = time rate of change of instantaneous frequency; and $A_{max}$ = the maximum amplitude of the excitation signal.

If the input signal c(t) refers directly to the temperature of the heating element 12, then $A_{max}$ will be in units of temperature. Assuming a substantially linear relationship between applied voltage and temperature, $A_{max}$ may alternatively be in units of Volts applied by the drive circuit 16 to the heating element 12.

As FIG. 3a also shows, the excitation signal may also include "quiet" periods during which no heat (other than any residual heat of the heating element 12 in the absence of excitation voltage) is applied to the blood via the heating element 12. The period of the heat signal may be changed according to the particular application, as may be the relative lengths of the "active" and "quiet" signal periods. As is well known from Fourier analysis, increasing the length of the "quiet" periods (in which the amplitude of the excitation signal is substantially zero) will have the effect of increasing the "spacing" of the frequency components of the input signal over its spectrum.

It is not necessary to include any "quiet" (partial) periods at all; rather, referring to FIG. 3a, it is possible to set $t_{n-1} = t_1$, so that the input signal will be continuously sinusoidal. Note that, whether or not the input signal includes "quiet" or "zero-amplitude" partial periods, the input signal according to the invention may be made "smooth", so that it is never necessary for the heating element to approximate a step increase or decrease in temperature as in code-based systems. In other words, the input signal used in this invention preferably is, or at least closely approximates, a function that is everywhere differentiable.

One way of generating an input signal as shown in FIG. 3a is to implement the drive circuit as a constant voltage connected as the input to an integrator, which in turn drives a voltage-controlled oscillator (VCO). A voltage regulation circuit, which may be the processor, possibly via a conventional digital-to-analog (D/A) converter (which may also be contained in the drive circuit 16), then selects the amplitude of the input to the integrator and thereby controls the rate of frequency shift of the VCO. "Quiet" periods for the input signal may then be created simply by resetting the integrator in a conventional manner (using a conventional, variable timing circuit or the processor) and clamping its input to ground. Generation of the input signal to the drive circuit 16 may, however, be accomplished digitally within the processor 18.

According to the invention, for example, the drive circuit includes a D/A converter, which is connected directly to an output of the processor 18. The processor 18 thereby outputs a sequence of numerical values corresponding to a digitized representation of the heat input signal c(t). This representation may be generated internally by the processor either through direct calculation of expression Eqn. 1 at each of a plurality of time steps over each period of the input signal, or by using some other known formula or table of values pre-stored in the memory 28.

Conventional input systems such as a keyboard, dials, etc., may also be connected to the processor in order to allow the user to enter such signal parameters as the minimum and maximum frequency values $f_0$ and $f_1$, the time period of the "sweep" of the input signal ($t_0$ and $t_1$), as well as the length of any "quiet" periods between active partial signal periods.

Figure 3B:
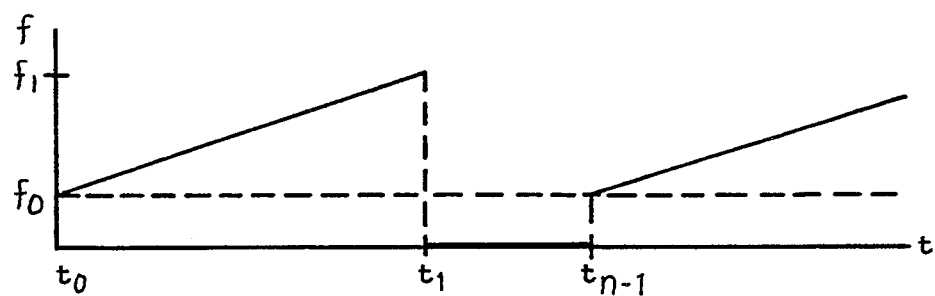

FIG. 3b illustrates the preferred linear frequency shift of the input signal. Although FIG. 3b illustrates a linearly increasing frequency, it will in general be just as easy to implement and use an input signal that has a linearly decreasing frequency.

Figure 4A:
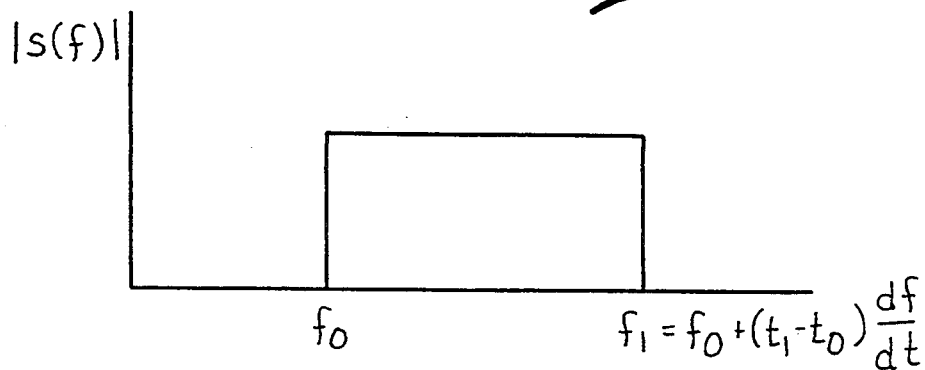
FIGS. 4a, 4b, and 4c illustrate, respectively, the frequency response, delay, and phase characteristics of a dispersive filter matched to the heat input signal shown in FIGS. 3a and 3b.
Figure 4B:
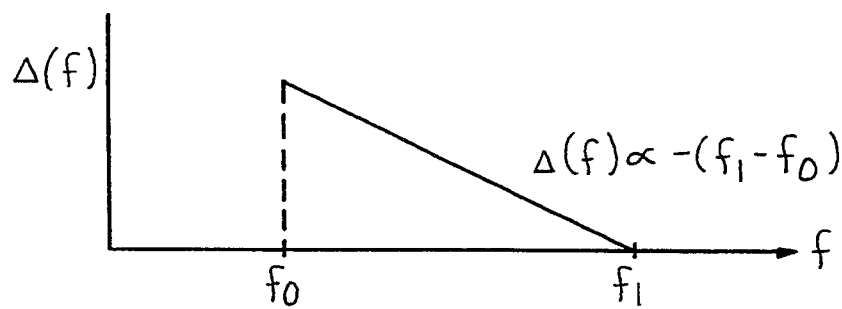
Figure 4C:
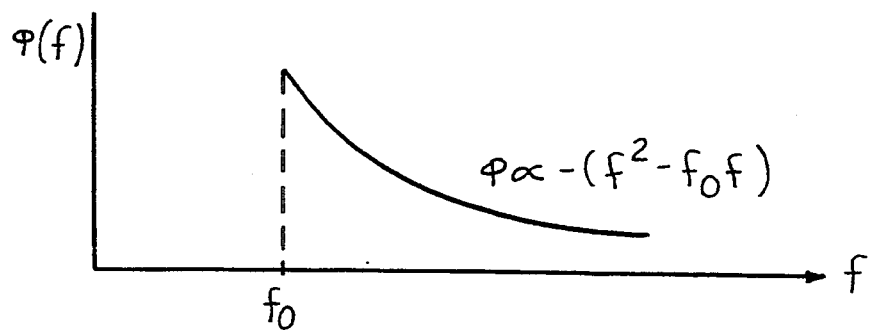

As FIG. 2 illustrates, the dispersive filter 22 is matched to the input signal in such a way that it compresses the energy of the input signal into a pulse. FIGS. 4a, 4b, and 4c illustrate graphically the amplitude, delay, and phase, respectively, of a dispersive filter that is matched to the input signal shown in FIGS. 3a and 3b.

As FIG. 4a illustrates, the spectrum of the dispersive filter 22 is substantially flat between the initial frequency $f_0$ and the highest input frequency $f_1$. Although a perfectly flat spectrum between $f_0$ and $f_1$ is unrealizable in practice, as is discussed below, the invention is able to approximate a flat spectrum much better than conventional coded techniques. As FIG. 4b shows, the delay of the filter is proportional to the negative of the difference between the instantaneous signal frequency and the initial frequency $f_0$.

By comparing FIG. 4b with FIGS. 3a and 3d, one can see that the first portion of the input signal (near time $t_0$), which has lower frequencies (near $f_0$), is delayed by the dispersive filter longer than the higher-frequency portion of the input signal (near time $t_1$). By matching the proportionality factor of the linear delay of the dispersive filter to the proportionality factor of linear increase of the frequency of the input signal, each frequency component in the input signal will be delayed by the amount necessary for all input frequencies to "arrive" at the output of the dispersive filter at the same time. This is equivalent to compressing the input signal into a pulse.

The delay of the dispersive filter 22 will, for the input signal illustrated in FIGS. 3a and 3b, take the following form:

$$\Delta = T - (f - f_0)/(df/dt), \text{ for } f_0 \leq f \leq f_1$$

where:

$\Delta$ is the delay time; and
$T = t_{max} - t_{min}$.

Finally, FIG. 4c illustrates the phase characteristic $\phi(f)$ of the dispersive filter as a function of frequency. As FIG. 4c shows, the phase characteristic of the dispersive filter for linear delay is second-order.

FIGS. 4a, 4b, and 4c show the frequency, delay, and phase characteristics of the dispersive filter used in the preferred embodiment of the invention. The actual frequency band [$f_0$, $f_1$] for the filter, the maximum spectral amplitude (at least approximately constant), and the speed and direction of frequency sweep will depend on the thermal, electrical and mechanical requirements of any given application and can be chosen using normal design methods.

Since a filter is defined by its frequency and phase response, and since the frequency range and amplitudes will be determined by the particular application, known analog or digital filter design techniques may be used to implement a corresponding analog or digital filter as soon as one decides on what particular components one wants to use in a given application of the invention. An example of a suitable implementation of the dispersive filter is described below.

Figure 5:
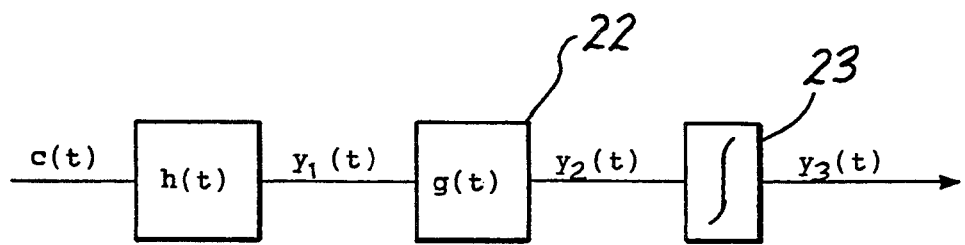
FIG. 5 illustrates the commutative property of certain functions of the system, as well as the relationship between corresponding signals.

According to the invention, the excitation signal c(t) is therefore preferably a wave form that "sweeps" linearly between two frequencies f1 and f2. Referring to FIG. 5, the system in which the fluid flows, which may be the cardiac system in which blood is flowing, represents a physiological channel that has an impulse response h(t). The broad-band wave form of the excitation signal c(t) stimulates this physiological channel. The output $y_1(t)$ of the physiological channel, which corresponds to the voltage of the thermistor 14 (see FIG. 1), is passed through the dispersive filter 22, which has an impulse response g(t) and produces an output signal $y_2(t)$.

As is illustrated in FIG. 4b, the dispersive filter preferably has a linear delay-versus-frequency characteristic such that it matches the linear frequency-versus-time characteristics of the excitation signal c(t). The output of the dispersive filter, which, in FIG. 5, is shown as $y_2(t)$, passes through the integrator 23 to form the output signal $y_3(t)$. As is shown below, the output of the integrator 23 is directly proportional to the area under the impulse response curve h(t), which is known to be inversely proportional to cardiac output.

Assuming that the systems h(t) and g(t) are linear, their order can be interchanged for purposes of analysis without changing the characteristics of the output signal $y_3(t)$. Note that the first operation is the convolution of the excitation signal c(t) with g(t). By choosing the delay response of the dispersive filter, that is, of g(t), to match the frequency sweep of the excitation signal, the output of the first convolution is a single impulse; in other words, all of the energy in the excitation signal c(t) is concentrated into a short time interval.

The impulse then excites the linear system h(t), which by definition responds with its impulse response. The final step is the integration of this impulse response, with the net result being the desired indication of cardiac output.

This can be shown mathematically as follows:

$$y_1(t) = c(t) * h(t)$$
$$= \int h(\tau)c(t - \tau)d\tau$$

where "*" is the convolution operator.
Thus:

$$y_2(t) = y_1(t)*g(t)$$
$$= \int y_1(\tau)g(t - \tau)d\tau$$
$$= \int \int h(\alpha)c(\tau - \alpha)d\alpha g(t - \tau)d\tau$$
$$= \int h(\alpha)\int c(\tau - \alpha)g(t - \tau)d\tau d\alpha$$

Now recall the definition of a dispersive filter as used in the invention:

$$\int c(\tau - \alpha)g(t - \tau)d\tau = \delta(t - \alpha)$$

where $\delta(t)$ = the Dirac function, that is, a pulse at X16me t. In other words, the dispersive filter compresses the input signal energy into a pulse. This then leads to the following further derivation:

$$y_2(t) = \int h(\alpha)\delta(t - \alpha)d\alpha$$
$$= h(t)$$

Although the input signal c(t) discussed above is shown as having a frequency that increases linearly, other signal profiles are possible. For example, the input signal (the temperature profile of the heating element 12), could begin at the highest frequency and then decrease linearly to a lowest frequency. A linear frequency sweep is preferred, however, because of ease of implementation and analysis. Moreover, it is not necessary for the rate of change of the frequency to be constant; in other words, the frequency shift need not be linear. As is described above, by generating the input signal to have a linearly changing frequency simplifies the design of the dispersive filter and leads to an ability, through integration of the output signal from the dispersive filter 22, to be a direct measure of cardiac output. If non-linear input signals are used, the dispersive filter characteristics may be modified using conventional techniques to match this signal and provide a "compressed" pulse as an output signal.

In applications in which cardiac output is to be measured, a typical time period and frequency range for blood flow analysis is a 10-second pulse from 1.0 to 10.0 Hz. This would result in a compressed pulse period of 1/9=0.111 seconds and an amplitude ratio (output to input) of 90. Assuming that heat is used as the measurement medium, this means that a swept input signal having 1 Watt of heater power could be detected as readily as a continuously heated source that has $\sqrt{90} \approx 9.5$ Watts. The invention thus makes it possible to obtain measurements while employing a minimum of heater energy.

In applications involving determining blood flow, once the thermal impulse response of the cardiac system is determined using the invention as described above, the processor 18 (see FIG. 1) determines the blood flow using known techniques. One technique that is advantageous because of its proven theoretical and experimental accuracy involves calculating the known Stewart-Hamilton equations, which demonstrate that blood flow is inversely proportional to the area under the thermal impulse response of the channel. (See G. N. Stewart, "The Output of the Heart in Dogs," Am. J. Phisiol., 22:159-183; and W. F. Hamilton, et al., "Simultaneous Determination of the Pulmonary and Systemic Circulation Times in Man and of a Figure Related to Cardiac Output," Am. J. Phisiol., 84:338.) Note that the invention provides an estimate of the thermal impulse response.

Other methods that are less robust and accurate, even assuming a knowledge of the changing cross-sectional area of a blood vessel, involve calculating flow as a function of the "time of flight" of a marker, such as heat, between the heater and the thermistor. The invention may also be used in such systems, whereby time of flight is estimated as a function of the time between generation of the periodic heat signals by the heater and the pulse-like output signal from the dispersive filter.

Most applications of the invention will involve relatively low sweep frequencies (the maximum frequency will typically not need to be greater than a few tens of Hertz), so that the thermal lag of the heating element 12 will not seriously affect the ability of the element to generate the heat signal accurately. To take advantage of the low-frequency nature of the heat signal, one implementation of the dispersive filter 22 (see FIG. 1) makes use of the well-known discrete Fourier transform (DFT).

Figure 6:
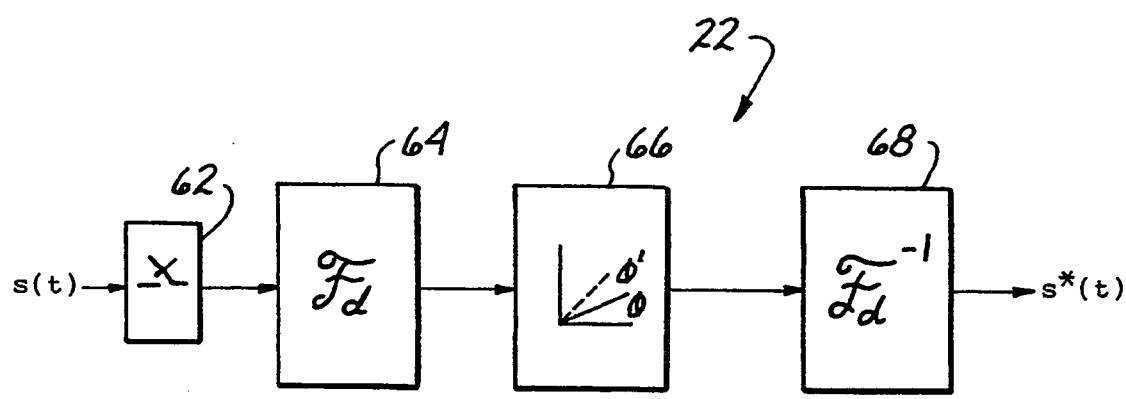
FIG. 6 is a block diagram of one embodiment of a dispersive filter that can be used in the invention.

FIG. 6 is a block diagram that illustrates an embodiment of the dispersive filter 22 that is based on DFT techniques. In FIG. 6, the sensed and (possibly) amplified heat signal from heating element forms an input signal s(t) to a sampling circuit 62, which samples the input signal N times with a sampling period T. The output from the sampling circuit 62 is applied to an N-point DFT transformation circuit 64, which may be any conventional device such as a known processor or a customized integrated circuit.

The DFT transformation circuit 64 either stores or receives from the sampling circuit 62 N sampled values of the input signal s(t). As is well known, the output from a DFT device such as the circuit 64 is a frequency-domain representation of the corresponding input; the output from the DFT is in the form of a series of magnitudes and phases. To implement the dispersive filter, the phases are modified (see below) by a phase adjustment circuit 66, which may also be a conventional programmable or hardwired device.

The phase-adjusted output signals from the phase adjustment circuit 66 are then transformed back into the time domain in an inverse DFT transformation circuit 68, which generates the dispersively filtered output signal s*(t). The inverse DFT circuit 68 may also be a conventional programmable or hardwired device.

In order to reduce design complexity and cost and to increase flexibility, any two or all three of the circuits 64, 66, and 68 may be implemented as a single conventional device with separate functional blocks or programmed routines. The sampling circuit 62 and associated memory storage circuitry (for storing sampled values) may also be included as a sub-circuit of any or all of the circuits 64, 66, and 68.

To illustrate the implementation of the dispersive filter 22 using the configuration shown in FIG. 6, assume that the excitation signal (the heat signal applied to blood flowing from the heart within a vessel), is applied such that it has a linear frequency sweep from f(t)=1 Hz to 10 Hz over a period of nine seconds. The delay, $\Delta(f)$, Fourier transformed impulse response, G(f), and phase, $\phi(f)$, will then be:

$$\Delta(f) = 10 - f$$

$$G(f) = 1 \cdot \exp[-2\pi j f \cdot \Delta(f)] = \exp[-2\pi j f \cdot (10f - f^2)]$$

$$\phi(f) = 2\pi \cdot (f^2 - 10f)$$

where $\exp[x] = e^x$ is the well-known exponential operator.

Now assume further a sampling rate of 50 Hz (T=1/50 s) for 20 s (long enough to capture the transducer output signal). This gives N=1000 samples at a sample spacing of 20 ms. Let $\Omega = (2\pi)/(NT)$. The discrete Fourier transform of the transducer signal s(t) is then computed using known numerical techniques by the transformation circuit 64 as:

$$S(f) = \sum_{m=0}^{N-1} s(nt) \cdot e^{-j\Omega Tnk}$$

or $$S(k) = \sum_{m=0}^{999} s(n) \cdot e^{-j\frac{2\pi n}{1000} k}$$

Each of these frequency-domain samples is a complex number, with a magnitude and a phase. The phase of each of these samples (complex points) is then rotated by the phase adjustment circuit 66 by adding:

$$\Phi'(f) = 2\pi (f^2 - 10f)$$

or $$\phi'(k) = 2\pi \left[ \left( \frac{2\pi k}{1000/50} \right)^2 - 10 \left( \frac{2\pi k}{1000/50} \right) \right]$$

The inverse DFT circuit 68 then uses known techniques to perform the inverse DFT transform:

$$f(nT) = \frac{1}{N} \cdot \sum_{k=0}^{N-1} \hat{S}(k\Omega) \cdot e^{+jTkn\Omega}$$

where S is the transform after phase adjustment.

Figure 7:
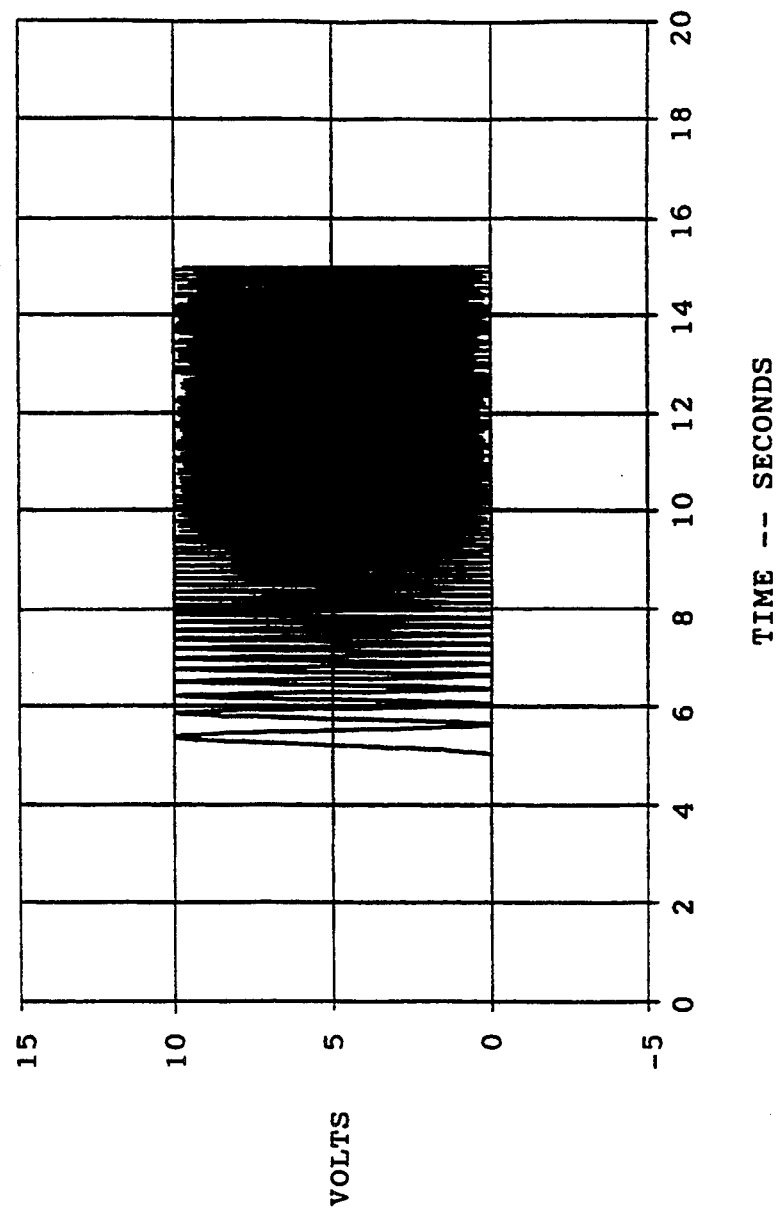
FIG. 7 is a plot of a simulated frequency-swept input signal according to the invention.

FIG. 7 is a plot of a simulated frequency-swept input signal used in a computer-simulated test of the invention. In the illustrated simulation, the total period of the input signal is 20 s ($0 \leq t \leq 20$). The active period, during which the heater is energized, is ten seconds ($5 \leq t \leq 15$), and the frequency increases linearly during this active period. The amplitude of the sinusoidal input signal is held at 10 Volts peak-to-peak. In FIG. 7, it is further assumed for purposes of simplicity only that the thermal lag of the heater is negligible.

Figure 8A:
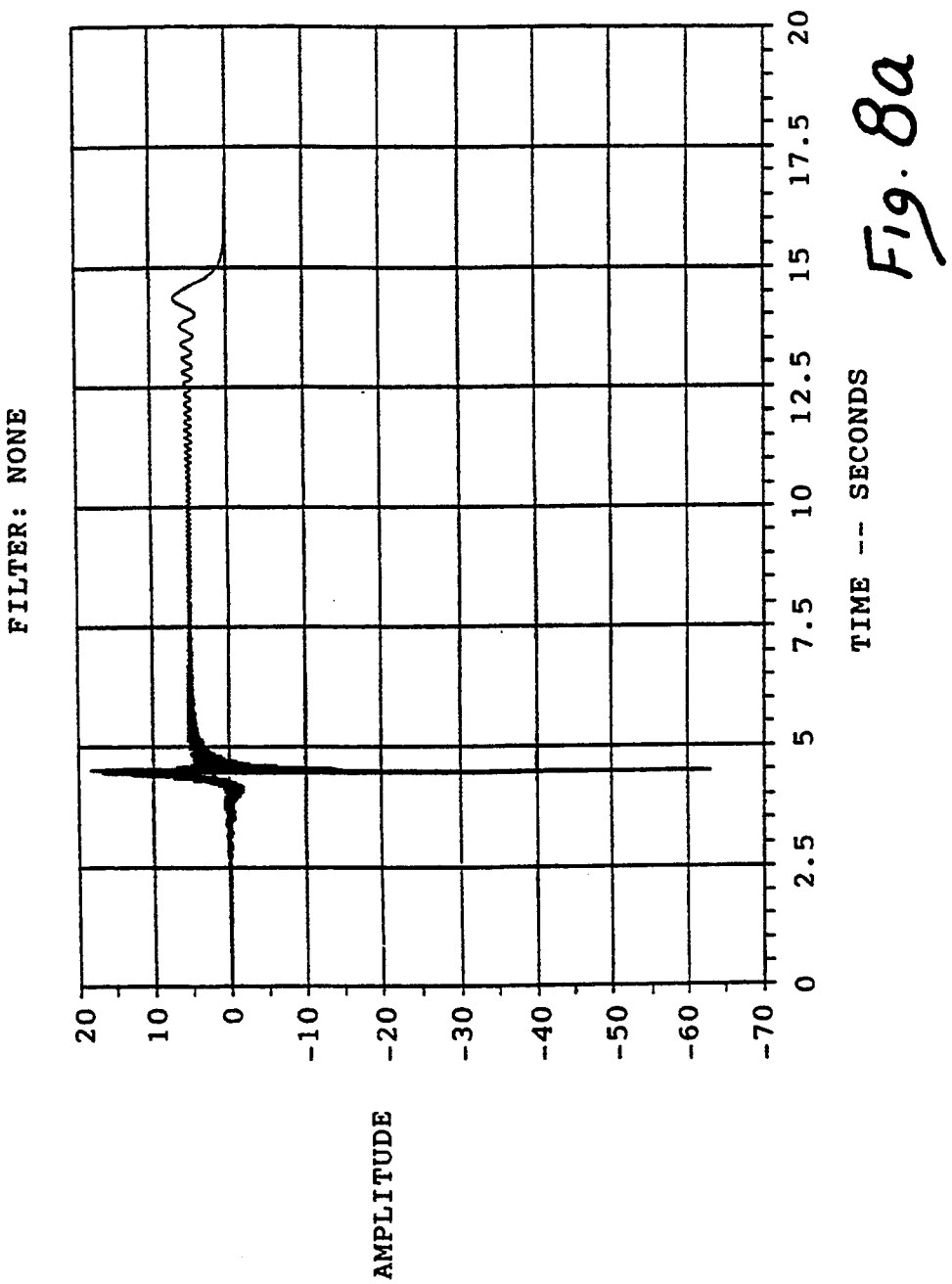

FIG. 8a is a plot of the simulated output signal from a dispersive filter according to the invention (designed in the manner discussed above), assuming that the channel through which the input signal of FIG. 7 passes has an all-pass frequency characteristic. In FIG. 8a, time is measured from the start of the active period of the input signal.

FIG. 8b shows on a larger scale the portion of the filtered output signal of FIG. 8a for $3.5 \leq t(\sec) \leq 5.5$. In other words, FIG. 8a illustrates the output of the invention for a channel with no frequency-dependent attenuation or lag in the channel. FIG. 8c is a plot of the frequency spectrum of the output signal shown in FIG. 8a.

Of course, the transmission characteristics of an actual signal channel such as a blood vessel will almost always display frequency-dependent attenuation and phase shifting; in other words, real channels will distort the heat signal depending on its frequency components. These effects will be reflected in the impulse response function of the channel. As an example, it is normally reasonable to assume that a fluid will act as a low-pass filter, especially in combination with a conventional heating element: Because of thermal lag in the fluid and heat transport within the fluid as it moves, impulsive or at least very rapid changes in temperature will normally appear to be "smoothed out" when they are sensed downstream; the temperature of the fluid cannot change fast enough to "keep up with" the input signal.

Figure 9A:
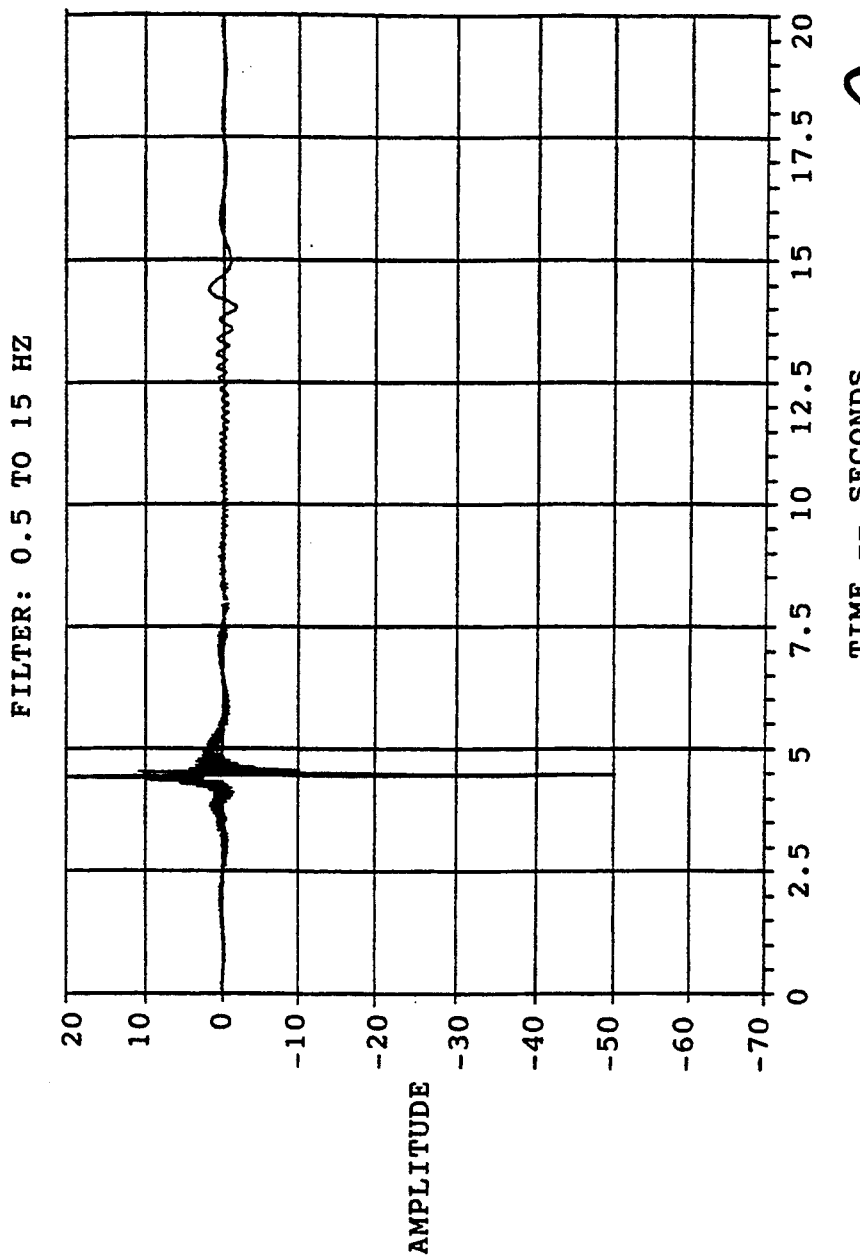
FIGS. 9a, 9b, and 9c.
Figure 9B:
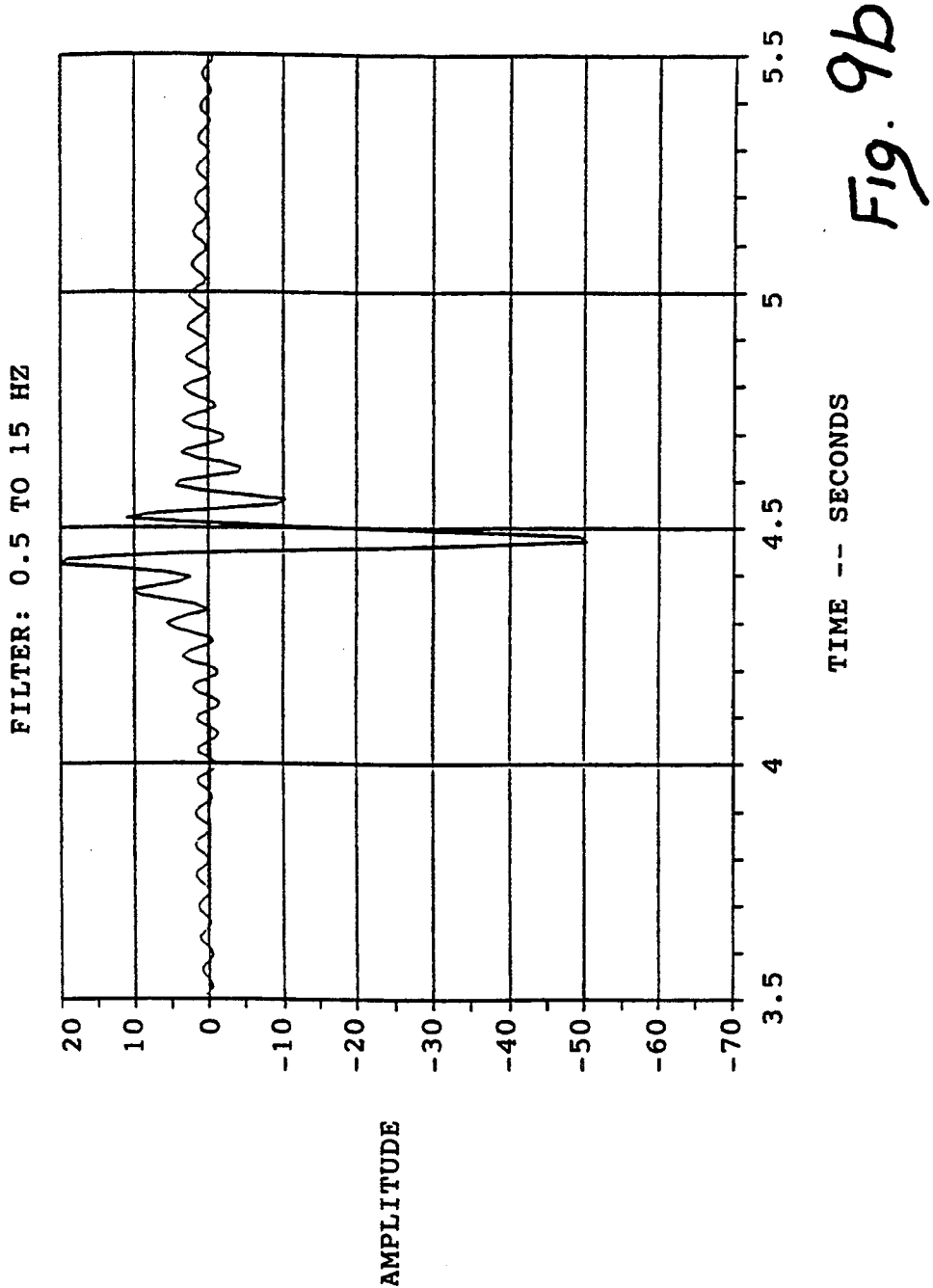
Figure 9C:
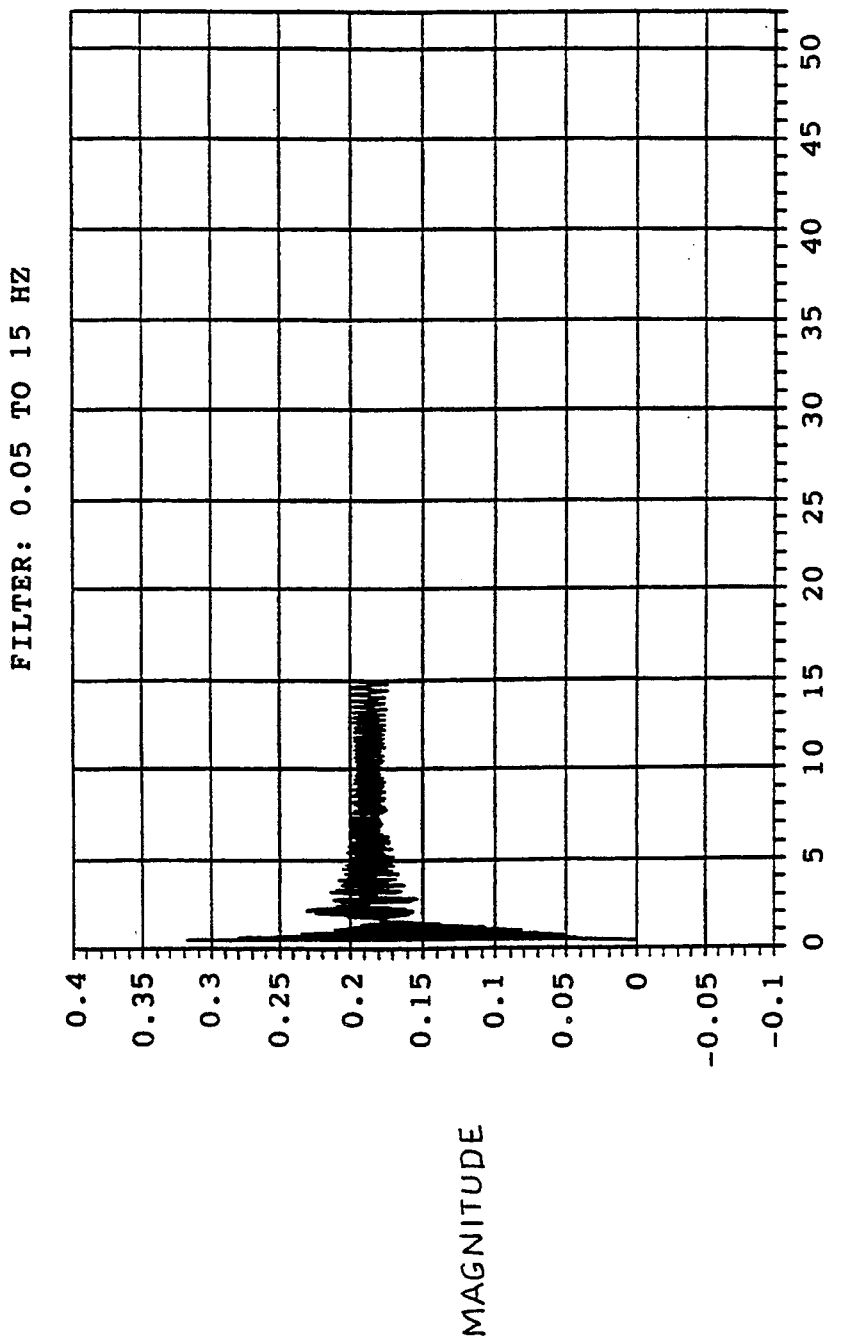
Figure 10A:
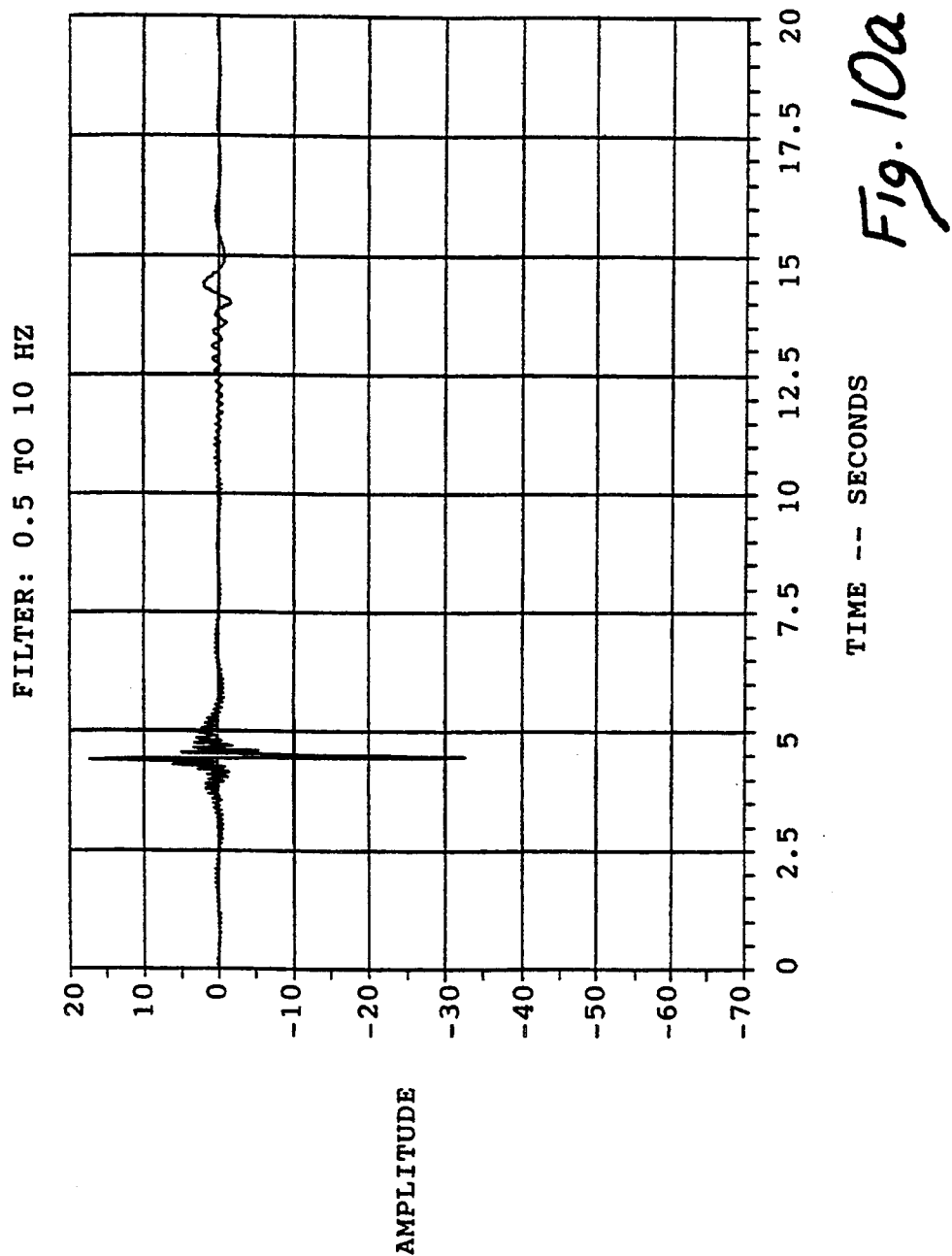
FIGS. 10a, 10b, and 10c.
Figure 10B:
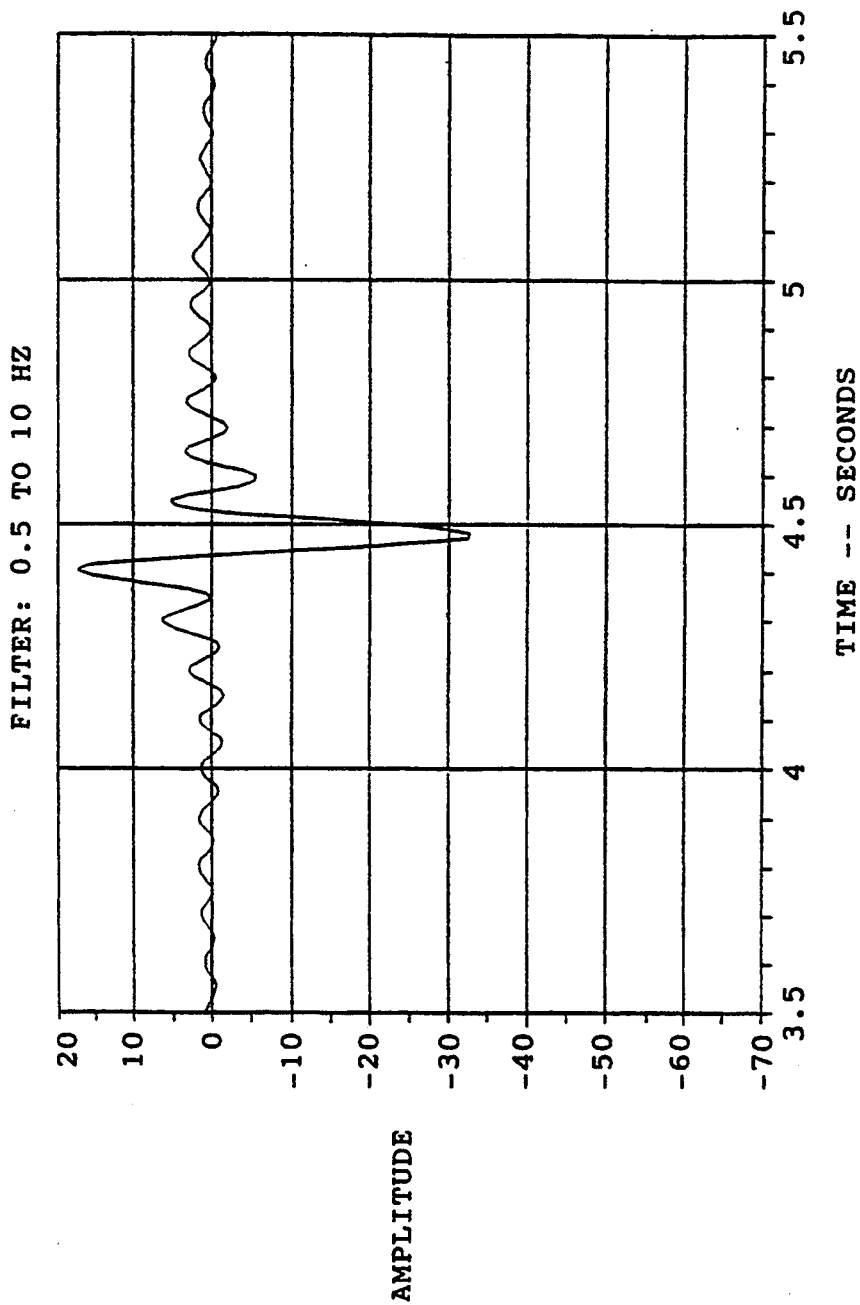
Figure 10C:
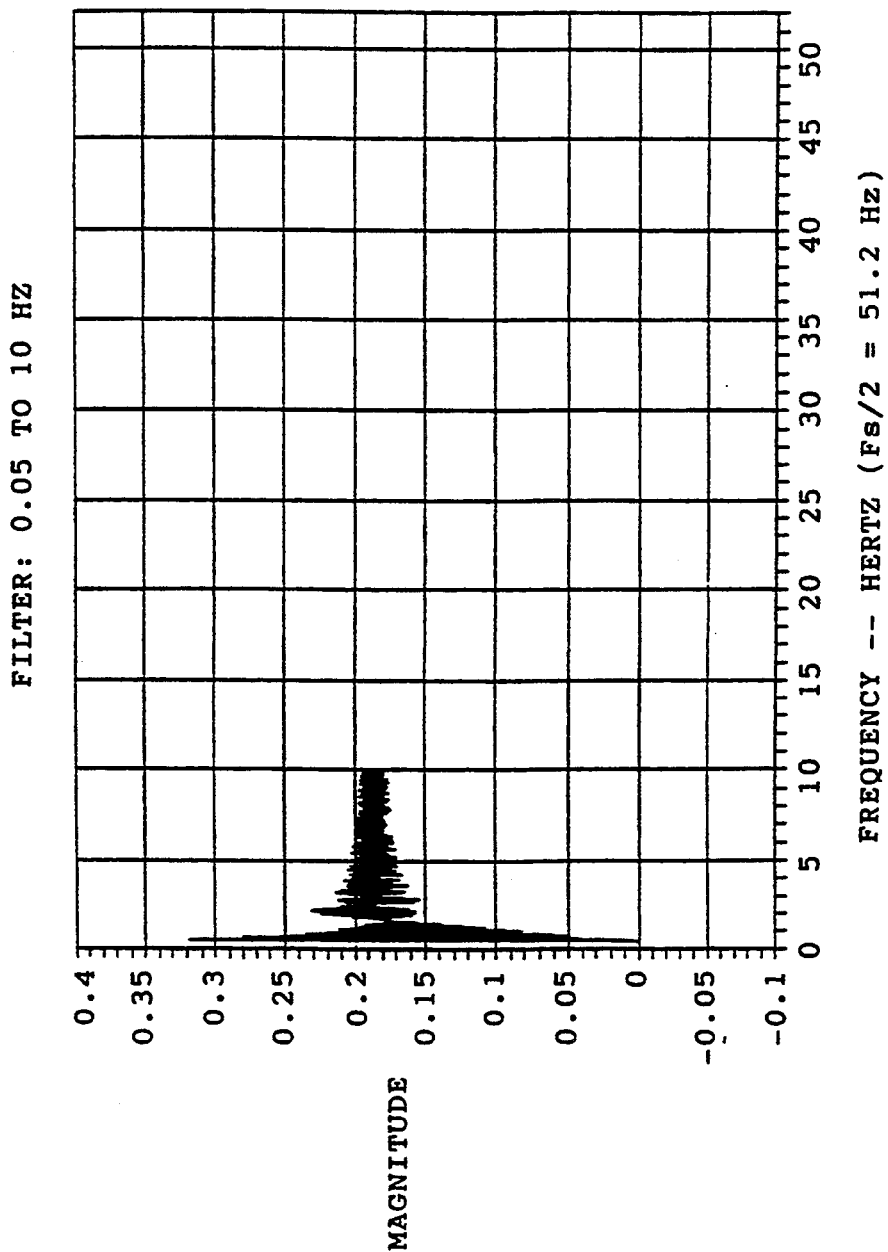
Figure 11A:
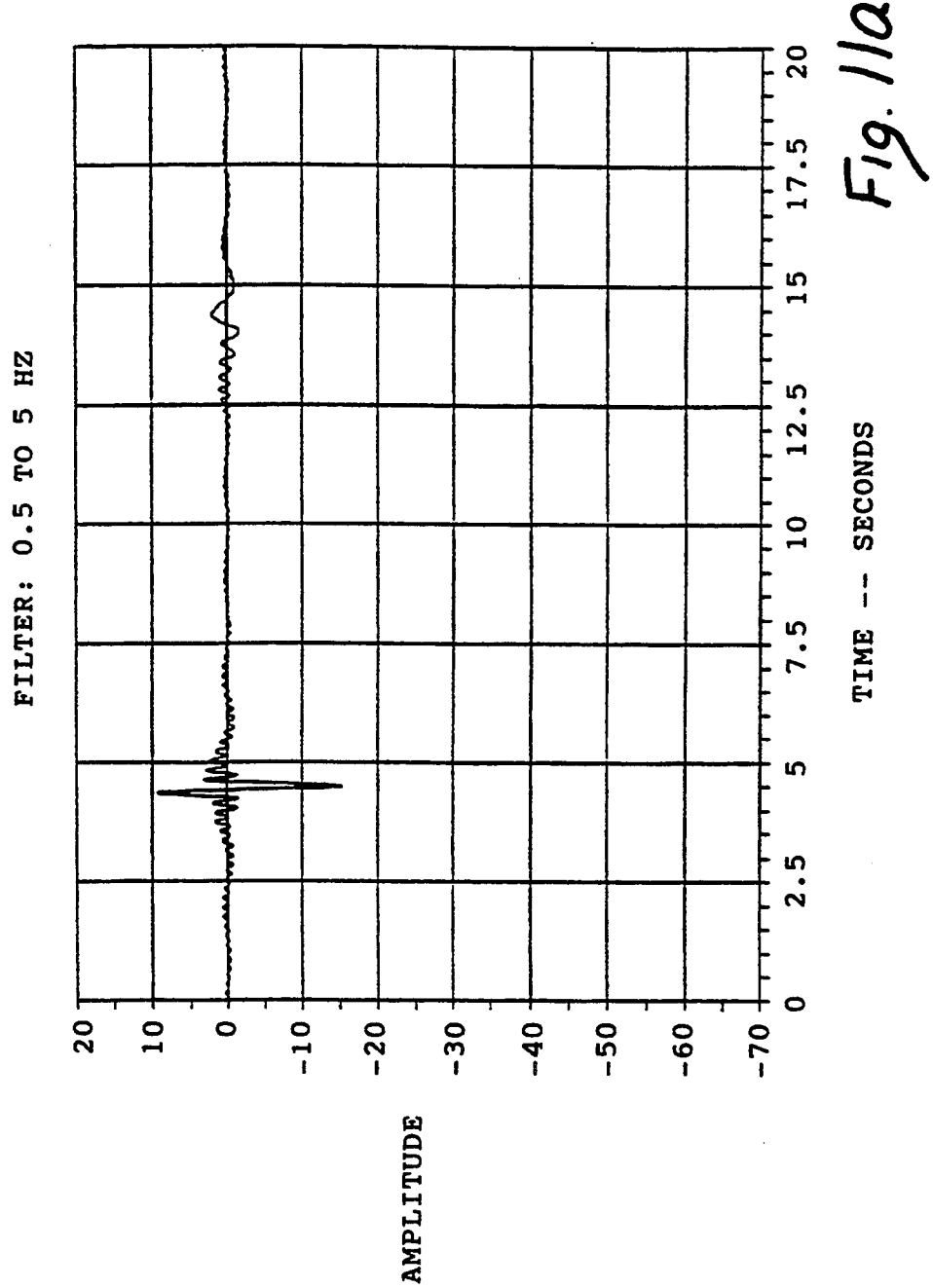
FIGS. 11a, 11b, and 11c are plots of the temporal and spectral characteristics of a simulated output signal from the invention after the input signal has passed through a simulated channel that is modelled as a bandpass filter that passes frequencies from 0.5 to 15.0 Hz, 0.05 to 10.0 Hz, and 0.5 to 5.0 Hz, respectively.
Figure 11B:
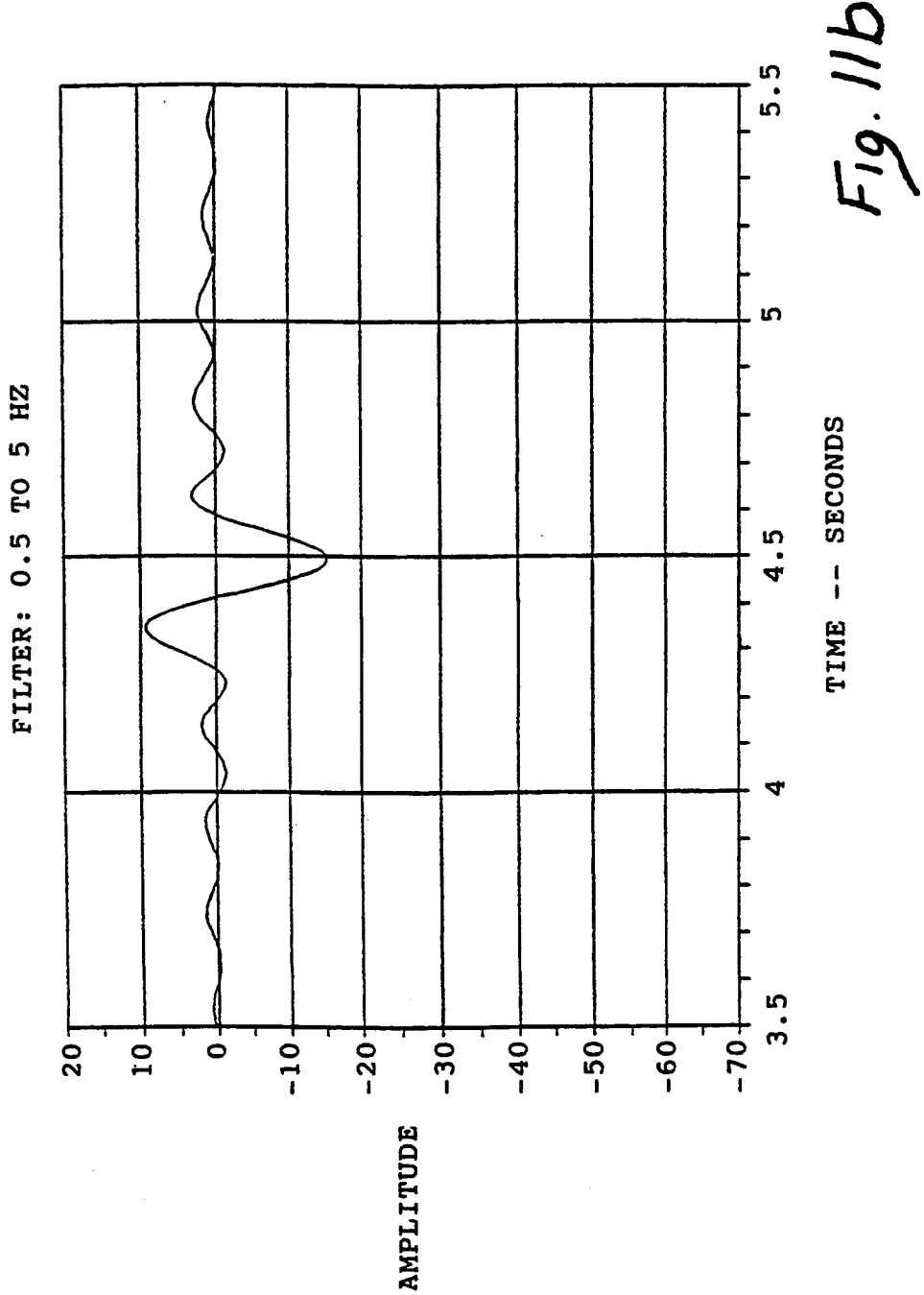
Figure 11C:
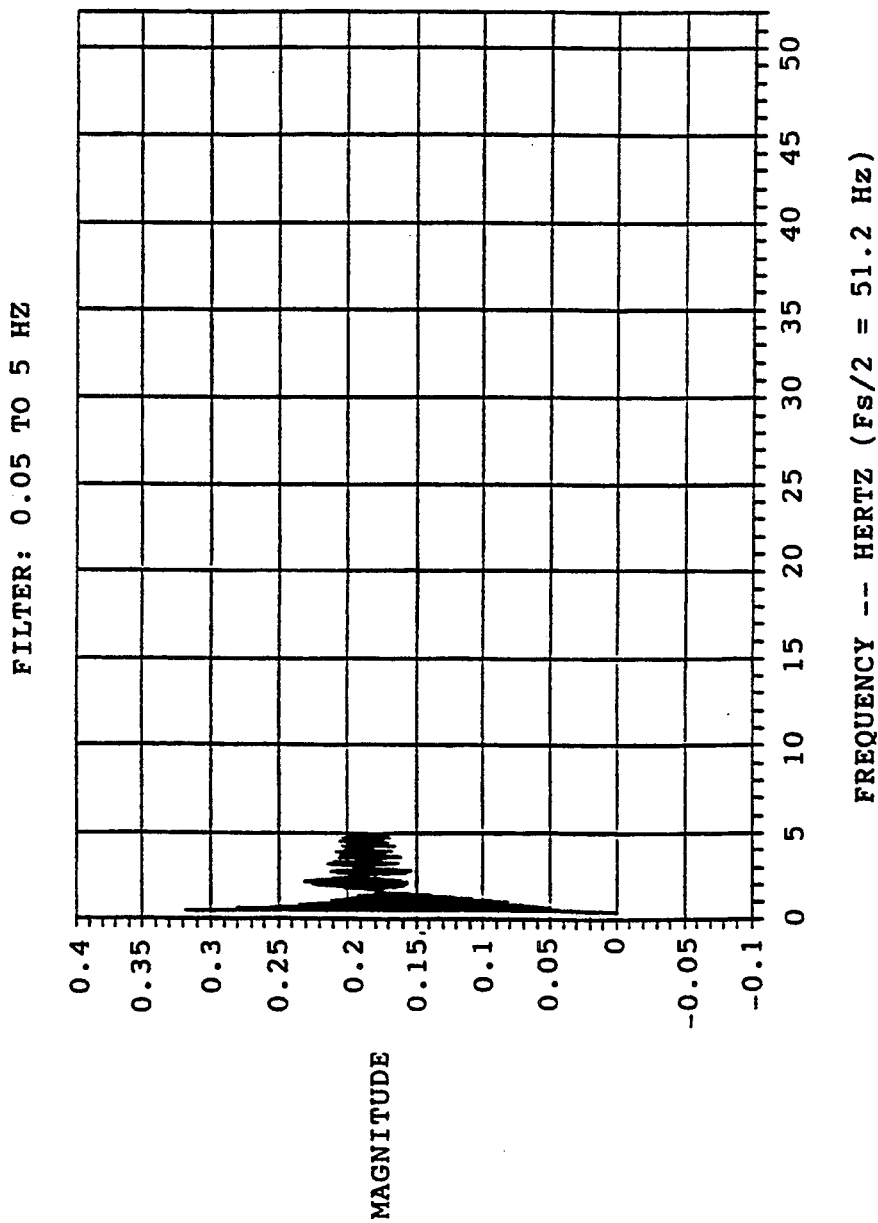

FIGS. 9a, 9b, and 9c, FIGS. 10a, 10b, and 10c, and FIGS. 11a, 11b, and 11c are plots of the temporal and spectral characteristics of a simulated output signal from the invention after the input signal has passed through a simulated channel that is modelled as a band-pass filter that passes frequencies from 0.5 to 15.0 Hz, 0.05 to 10.0 Hz, and 0.5 to 5.0 Hz, respectively. FIGS. 9a, 10a, and 11a show the respective output signals from the dispersive filter; FIGS. 9b, 10b, and 11b show the portions of these same signals for $3.5 \leq t(\sec) \leq 5.5$.; and FIGS. 9c, 10c, and 11c show the respective frequency spectra of these output signals.

First, the figures show the impulse-like (sin x)/x nature of the output signals from the dispersive filter. Second, the figures illustrate the amplitude reduction and time spreading of the output signal from the dispersive filter that is caused by the frequency-dependent effects of the channel. Comparing FIGS. 8b, 9b, 10b and 11b, one can see that band-pass (mostly low-pass) filtering—while not intended to model the physiological channel quantitatively—does illustrate how variations in the impulse response of the channel affect the shape of the output signal from the dispersive filter, and therefore the area under the output signal. As the Stewart-Hamilton equations show, this area (which is determined by the integrator 23) is inversely proportional to cardiac output.

The following table compares a frequency-swept system according to the invention with a code-based system such as that described in the Yelderman patent. A 10-second active signal period was used for the system according to the invention, with a continuous frequency shift from 0.1 Hz to 10 Hz. For the code system, a 15-bit maximal length code was used (giving 0.4 second per chip).

TABLE 1

|  | Code | Swept-frequency |
| --- | --- | --- |
| Period: | 6 s | 15 s |
| Correlation gain: | 15 | 90 |
| Bandwidth: | 2.5 Hz (1st null) | 9 Hz |
| Spectral distribution: | [sin(x)/x]$^2$ | rectangular |
| Delay resolution: | 0.4 s | 0.11 s |
| Frequencies in | 10 | 90 |

TABLE 1-continued

| Code | Swept-frequency |
|---|---|
| spectrum: | |

Note particularly that the invention is able to include in the spectrum nine times as many frequencies as the code system. As is mentioned above, this greatly reduces the impact of particular frequency components of noise within the bandwidth of the system.

As can be shown, for example, using the equations given in *Spread Spectrum Systems*, Robert C. Dixon, 2nd ed., John Wiley & Sons, 1984, pp. 44–7, the theoretical ratio between output power $P_o$ and input power $P_i$ for the swept-frequency system according to the invention is:

$$P_o/P_i = \Delta T \cdot \Delta f = (t_1 - t_0) \cdot (f_1 - f_0) = 90$$

for the test system whose results are given in Table 1 above. As was indicated above, the corresponding ratio for a maximal-length code system is only approximately 0.5.

Other advantages of the invention are:
1. all signals used are continuous, as opposed to the discontinuous, square-wave waveforms needed for heating using, for example, a pseudo-random code;
2. the frequency-swept signals used in the invention have a more continuous frequency spectrum than code-based systems;
3. even though the signal-to-noise ratio of the invention is higher than conventional systems such as code-based systems, the peak-to-average power of the heat signal used in the invention is typically lower; this means that more total heat (the "signal") can be applied to sensitive cardiac areas such as in or near an atrium or the pulmonary artery without having to have as high a peak temperature;
4. because the invention excites the physiological channel with energy spread over a broad spectral bandwidth, it is less vulnerable to sources of interference that are narrow-band in nature (such as a ventilator);
5. time delay is an inherent part of the measurement in the system according to the invention;
6. the compression gain using frequency-swept signals as in the invention is typically better than the gain obtained using known code-based systems; and
7. the matched filter used in the invention is more easily implemented than the filters needed for code-based systems, which typically require correlation calculations.

We claim:

1. A system for measuring fluid flow within a conduit comprising:
    heating means for applying heat to the fluid at an upstream position as a series of periodic heat signals;
    temperature-sensing means located at a downstream position for measuring a local temperature of the fluid and for generating an electrical fluid temperature signal corresponding to the local temperature;
    filter means, having a filtered output signal, connected to the temperature-sensing means for sensing the presence of the periodic heat signals at the downstream position;
    processor means, connected to the filter means, for calculating fluid flow as a predetermined function of the filtered output signal;
    in which:
    each periodic heat signal is sinusoidal and has an instantaneous frequency that varies substantially continuously between a first frequency and a second frequency over a predetermined active input signal period; and
    the filter means has a substantially pulse-shaped output signal when the periodic heat signal is applied as an input signal to the filter means.

2. A system as defined in claim 1, in which the heating means comprises means for varying the instantaneous frequency of each periodic heat signal linearly between the first and second frequencies over the active input signal period.

3. A system as defined in claim 2, in which the filter means has a frequency response with substantially constant amplitude between the first and second frequencies and a substantially linear delay characteristic between the first and second frequencies.

4. A system as defined in claim 3, in which:
    during each active signal period, the periodic heat signal has the form:

$$A_{max} \cdot \cos\{2\pi \cdot f(t) \cdot (t - t_{min}) + \phi\}, \text{ for } t_{min} \leq t \leq t_{max}$$

where:
    $A_{max}$ is a maximum amplitude;
    $f(t) = f_0 + t \cdot df/dt$;
    $f_0$ is the first frequency;
    t is a measurement time after an initial signal time $t_{min}$;
    df/dt is a time rate of change of the instantaneous frequency;
    the delay characteristic of the filter means from the first frequency to the second frequency has the form:

$$\Delta = T - (f - f_0)/(df/dt), \text{ for } f_0 \leq f \leq f_1$$

where:
    $\Delta$ is the delay time;
    $T = t_{max} - t_{min}$; and
    $f_1$ is the second frequency.

5. A system as defined in claim 1, in which the heating means comprises means for applying the periodic heat signals to include inactive input periods during which an amplitude of the periodic heat signals is substantially zero degrees above an ambient fluid temperature at the upstream position.

6. A system as defined in claim 1, in which the heating means includes a resistive heating element and a drive circuit for applying electrical current to the resistive heating element.

7. A system as defined in claim 6, in which:
    the processor means is electrically connected to the heater drive circuit;
    the processor means includes heat profile generation means for applying to the heater drive circuit an electrical activation signal corresponding to the periodic heat signals.

8. A system as defined in claim 7, in which the processor means includes a memory means for pre-storing a pre-determined heat signal profile corresponding to the periodic heat signals.

9. A system as defined in claim 1, in which the temperature-sensing means is a thermistor.

10. A system as defined in claim 1, in which the filter means includes signal integration means for forming an integrated output signal corresponding to the integral of an estimated channel transfer function of the fluid within the conduit from the upstream position to the downstream position.

11. A system as defined in claim 1, in which:
the heating means is adapted to be located within the right atrium of the heart of a patient; and
the temperature-sensing means is adapted to be located within the pulmonary artery of the patient.

12. A system for measuring cardiac output comprising:
heating means for applying heat to blood at an upstream position as a series of periodic heat signals;
temperature-sensing means including a thermistor located at a downstream position for measuring a local temperature of the blood and for generating an electrical blood temperature signal corresponding to the local temperature;
filter means, having a filtered output signal, connected to the temperature-sensing means for sensing the presence of the periodic heat signals at the downstream position;
processor means, connected to the filter means, for calculating blood flow as a predetermined function of the filtered output signal;
in which:
the upstream position is located within the right atrium of the heart of a patient;
the downstream position is located within the pulmonary artery of the patient;
the heating means includes a resistive heating element and a drive circuit means for applying electrical current to the resistive heating element;
each periodic heat signal is sinusoidal and has an instantaneous frequency that varies substantially continuously between a first frequency and a second frequency over a predetermined active input signal period;
the instantaneous frequency of each periodic heat signal varies linearly between the first and second frequencies over the active input signal period;
the periodic heat signals include inactive input periods during which an amplitude of the periodic heat signals is substantially zero degrees above an ambient blood temperature at the upstream position;
the processor means is electrically connected to the heater drive circuit means;
the processor means includes heat profile generation means for applying to the heater drive circuit means an electrical activation signal corresponding to the periodic heat signals;
the filter means includes signal integration means for forming an integrated output signal corresponding to the integral of an estimated cardiac channel transfer function from the upstream position to the downstream position;
the filter means has a frequency response with substantially constant amplitude between the first and second frequencies and a substantially linear delay characteristic between the first and second frequencies; the filter means has a substantially pulse-shaped output signal when the periodic heat signal is applied as an input signal to the filter means; and
during each active signal period, the periodic heat signal has the form:

$$A_{max} \cdot \cos\{2\pi \cdot f(t) \cdot (t - t_{min}) + \phi\}, \text{ for } t_{min} \leq t \leq t_{max}$$

where:
$A_{max}$ is a maximum amplitude;
$f(t) = f_0 + t \cdot df/dt$;s
$f_0$ is the first frequency;
t is a measurement time after an initial signal time $t_{min}$;
df/dt is a constant time rate of change of the instantaneous frequency;
the delay characteristic of the filter means from the first frequency to the second frequency has the form:

$$\Delta = T = (f - f_0)/(df/dt), \text{ for } f_0 \leq f \leq f_1$$

where:
$\Delta$ is the delay time;
$T = t_{max} - t_{min}$; s and
$f_1$ is the second frequency.

13. A method for measuring fluid flow within a conduit including the following steps:
A) heating the fluid at an upstream position according to a periodic heat profile signal that is sinusoidal and has an instantaneous frequency that varies substantially continuously between a first frequency and a second frequency over a pre-determined active input signal period;
B) sensing a local temperature of the fluid at a downstream position and generating an electrical fluid temperature signal corresponding to the local temperature;
C) in a filter, generating a substantially pulse-shaped output signal upon sensing the presence of the periodic heat profile signal at the downstream position; and
D) calculating fluid flow as a predetermined function of the pulse-shaped output signal.

14. A method as defined in claim 13, in which the step of calculating fluid flow includes the step of calculating the integral of the pulse-shaped output signal.

15. A method as defined in claim 14, in which the step of calculating fluid flow includes the step of generating a fluid flow signal that is inversely proportional to the integral of the pulse-shaped output signal.

16. A method as defined in claim 13, in which the continuous variation of the periodic heat profile signal is linear.

17. A method as defined in claim 16, further including the following steps:
A) generating the periodic heat profile signal with the form:

$$A_{max} \cdot \cos\{2\pi \cdot f(t) \cdot (t - t_{min}) + \phi\}, \text{ for } t_{min} \leq t \leq t_{max}$$

where:
$A_{max}$ is a maximum amplitude;
$f(t) = f_0 + t \cdot df/dt$;
$f_0$ is the first frequency;
t is a measurement time after an initial signal time $t_{min}$;
df/dt is a constant time rate of change of the instantaneous frequency;
B) generating an electrical temperature signal corresponding to the local temperature of the fluid; and
C) filtering the electrical temperature signal with a delay characteristic in a frequency range $f_0 \leq f \leq f_1$ with the following form:

$$\Delta = T - (f - f_0)/(df/dt)$$

where:
$\Delta$ is the delay time;
$T = t_{max} - t_{min}$; and
$f_1$ is the second frequency.

* * * * *